United States Patent
Bramanti et al.

(10) Patent No.: US 9,702,848 B2
(45) Date of Patent: Jul. 11, 2017

(54) MEASUREMENT OF LACTIC ACID IN BIOLOGICAL FLUIDS

(71) Applicant: POWER FIT S.R.L., San Giuliano Terme (PI) (IT)

(72) Inventors: Emilia Bramanti, Pietrasanta (IT); Fabrizio Zucchini, San Giuliano Terme Pisa (IT); Massimo Onor, Sarzana (IT); Vincenzo Di Muro, Pietrasanta (IT)

(73) Assignee: POWER FIT S.r.l., San Giuliano Terme (PI) (IT)

(*) Notice: Subject to any disclaimer, the term of this patent is extended or adjusted under 35 U.S.C. 154(b) by 49 days.

(21) Appl. No.: 14/954,422

(22) Filed: Nov. 30, 2015

(65) Prior Publication Data

US 2016/0084795 A1 Mar. 24, 2016

Related U.S. Application Data

(62) Division of application No. 14/345,595, filed as application No. PCT/EP2012/068867 on Sep. 25, 2012, now Pat. No. 9,234,887.

(30) Foreign Application Priority Data

Sep. 28, 2011 (IT) .................. PI2011A0104
Jan. 25, 2012 (IT) .................. PI2012A0012

(51) Int. Cl.
*G01N 33/50* (2006.01)
*G01N 33/48* (2006.01)
(Continued)

(52) U.S. Cl.
CPC ....... *G01N 27/4168* (2013.01); *G01N 21/251* (2013.01); *G01N 21/33* (2013.01);
(Continued)

(58) Field of Classification Search
CPC .. G01N 21/251; G01N 21/33; G01N 21/6428; G01N 21/76; G01N 21/78;
(Continued)

(56) References Cited

U.S. PATENT DOCUMENTS

| | | | |
|---|---|---|---|
| 2,893,843 | A | 7/1959 | Adams, Jr. |
| 2,893,844 | A | 7/1959 | Cook |

(Continued)

FOREIGN PATENT DOCUMENTS

| | | |
|---|---|---|
| CN | 101639446 | 2/2010 |
| GB | 1522965 | 8/1978 |
| JP | 2007127422 | 5/2007 |

OTHER PUBLICATIONS

Tomas Perez-Ruiz et al.; "Flow injection determination of lactate based on a photochemical reaction using photometric and chemiluminescence detection"; The Analyst; vol. 124, No. 10; Oct. 1, 1999; pp. 1517-1521.*

(Continued)

*Primary Examiner* — Jennifer Wecker
(74) *Attorney, Agent, or Firm* — Stetina Brunda Garred & Brucker

(57) ABSTRACT

We propose a procedure for the determination of lactic acid or lactate in biological fluids, which is simple and low cost with respect to the known methodologies. This procedure can be used by unskilled personnel and it can be implemented in disposable test strips and portable measure devices. The procedure is based on the photochemical reaction of lactic acid with Fe(III), which is reduced to Fe(II) when irradiated with UV light. The Fe(II), produced proportionally to the amount of lactate in the sample, is determined electrochemically or using its reaction with a colored complexing agent, such as 1,10-phenanthroline, and determined by spectrophotometry. This method is advantageous (Continued)

both for the low cost of the reagents employed, and for their short and long term stability.

20 Claims, 4 Drawing Sheets

(51) Int. Cl.

| | | |
|---|---|---|
| G01N 33/00 | (2006.01) | |
| G01N 21/33 | (2006.01) | |
| G01N 21/25 | (2006.01) | |
| G01N 21/17 | (2006.01) | |
| G01N 27/00 | (2006.01) | |
| G01N 27/02 | (2006.01) | |
| G01N 27/30 | (2006.01) | |
| G01N 21/76 | (2006.01) | |
| G01N 21/78 | (2006.01) | |
| G01N 27/416 | (2006.01) | |
| G01N 33/487 | (2006.01) | |
| G01N 21/64 | (2006.01) | |
| G01N 21/84 | (2006.01) | |
| G01N 27/327 | (2006.01) | |
| G01N 33/52 | (2006.01) | |
| G01N 21/55 | (2014.01) | |

(52) U.S. Cl.
CPC ......... *G01N 21/6428* (2013.01); *G01N 21/76* (2013.01); *G01N 21/78* (2013.01); *G01N 21/8483* (2013.01); *G01N 27/327* (2013.01); *G01N 27/3272* (2013.01); *G01N 27/3277* (2013.01); *G01N 33/48707* (2013.01); *G01N 33/52* (2013.01); *Y10T 436/201666* (2015.01)

(58) Field of Classification Search
CPC ............. G01N 21/8483; G01N 27/327; G01N 27/3272; G01N 27/3277; G01N 27/4168; G01N 33/48707; G01N 33/52; Y10T 436/201666
See application file for complete search history.

(56) References Cited

U.S. PATENT DOCUMENTS

| | | |
|---|---|---|
| 2,912,309 A | 11/1959 | Free |
| 3,008,879 A | 11/1961 | Harvill |
| 3,092,465 A | 6/1963 | Adams, Jr. et al. |
| 3,298,739 A | 1/1967 | Scruggs |
| 3,418,083 A | 12/1968 | Hans-Georg et al. |
| 3,418,099 A | 12/1968 | Carter et al. |
| 3,573,171 A | 3/1971 | Green |
| 3,798,064 A | 3/1974 | Amoser |
| 3,802,842 A | 4/1974 | Lange et al. |
| 3,915,647 A | 10/1975 | Wright |
| 3,917,453 A | 11/1975 | Milligan et al. |
| 3,933,594 A | 1/1976 | Milligan et al. |
| 3,936,357 A | 2/1976 | Milligan et al. |
| 3,992,158 A | 11/1976 | Przybylowicz et al. |
| 4,254,222 A | 3/1981 | Owen |
| 4,467,811 A | 8/1984 | Clark, Jr. |
| RE32,016 E | 10/1985 | Esders et al. |
| 5,757,002 A | 5/1998 | Yamasaki et al. |
| 5,759,796 A | 6/1998 | Azzoni et al. |
| 6,120,676 A | 9/2000 | Heller et al. |
| 7,319,018 B2 * | 1/2008 | Pandey ............... C12Q 1/001 204/403.04 |
| 7,476,202 B2 | 1/2009 | Raney et al. |
| 7,871,568 B2 | 1/2011 | Liang et al. |
| 2004/0141960 A1 | 7/2004 | Haeberlein et al. |
| 2009/0047177 A1 | 2/2009 | Walker et al. |

OTHER PUBLICATIONS

International Search Report and Written Opinion for International Application No. PCT/EP2012/068867; Nov. 13, 2012; 11 pages.

Perez-Ruiz T et al.; "High-performance liquid chromatographic separation and quantification of citric, lactic, malic, oxalic and tartaric acids using a post-column photochemical reaction and chemiluminescence detection"; Journal of Chromatography, Elsevier Science Publishers B.V, NL; vol. 1026, No. 1-2; Feb. 13, 2004; pp. 57-64.

Shimojo N et al.; "Electrochemical assay system with single-use electrode strip for measuring lactate in whole blood"; Clinical Chemistry, American Association for Clinical Chemistry, Washington, DC; vol. 39, No. 11; Jan. 1, 1993; pp. 2312-2314.

Fontella F U et al.; "Acute and repeated restraint stress influences cellular damage in rat hippocampal slices exposed to oxygen and glucose deprivation"; Brain Research Bulletin, Elsevier Science Ltd, Oxford, GB; vol. 65, No. 5; May 15, 2005; pp. 443-450.

Carlo Baldari et al.; "Accuracy, reliability, linearity of Accutrend and Lactate Pro versus EBIO plus analyzer"; European Journal of Applied Physiology, Springer, Berlin, DE.; vol. 107, No. 1; Jun. 14, 2009; pp. 105-111.

\* cited by examiner

MEASUREMENT OF LACTIC ACID IN BIOLOGICAL FLUIDS

The present application is a divisional patent application of U.S. patent application Ser. No. 14/345,595, filed on Mar. 18, 2014, which is a 371 of International Application No. PCT/EP2012/068867, filed on Sep. 25, 2012, which claims priority to Italian Application No. PI2011A000104, filed on Sep. 29, 2011 and Italian Application No. PI2012A000012, filed on Jan. 25, 2012, the entire contents of which are incorporated herein by reference.

SCOPE OF THE INVENTION

The present invention is related to kit and methods for the clinical analysis of lactic acid (or lactate) and, in particular, to the method for the determination of lactic acid (or lactate) in biological fluids, based on the redox reaction of a selective oxidant reagent. In particular, the redox reaction is activated by irradiation of the mixture biological fluid-oxidant with UV light.

TECHNICAL NOTE

Lactic acid (or lactate) is a product of anaerobic glicolyisis resulting from pyruvate by the enzyme lactate dehydrogenase (LDH). The lactic acid can be found in blood and biological fluids of human beings and animals.

A healthy adult man normally produces about 120 g of lactic acid a day. Among these, 40 g (33%) are produced by tissues characterized by an exclusively anaerobic metabolism (retina and blood red cells). The remaining 80 g (67%) are produced by other tissues (most of all muscle) on the basis of the actual oxygen availability. In liver lactic acid is reconverted into glucose (Cori cycle). Heart is able to metabolize lactic acid to produce energy.

The lactate/pyruvate molar ratio (L/P is a reliable marker of cell anaerobic/aerobic metabolism. Thus, the determination of lactate concentration level is a good approach to evaluate the balance between the oxygen demand of tissues and its use, and it is useful in the study of animal and cellular physiology.

The increase of lactic acid (lactic acidosis) can occur in two conditions:

a) hypoxia, i.e. the oxygen deficiency (lactic acidosis of type A, fast);

b) high rate of anaerobic glycolysis (lactic acidosis of type B, slow).

In type A lactic acidosis the aerobic pathway, i.e. the oxidation metabolic pathway of pyruvate to carbon dioxide and water, is blocked for several reasons. This occurs in inborn errors of the mitochondrial respiratory chain, in cardiovascular diseases (ischemia, hypoxemia, anemia) and in other diseases. In particular, oxygen deficits (tissue hypoxia) are the most common and often refractory causes of lactic acidosis, including pulmonary problems (low $PO_2$), circulatory problems (poor delivery of $O_2$), and hemoglobin problems (low $O_2$-carrying capacity, for various reasons).

In type B lactic acidosis, instead, the anaerobic glycolitic pathway proceeds at high rate, it causes low ATP concentration levels and the pyruvic acid produced accumulates and is reduced to lactic acid by LDH. This occurs during intense exertion and in all conditions of decoupling of oxidative phosphorilation, giving accumulation of lactate. For example this occurs in the deficiency of pyruvate dehydrogenase enzyme or in B1 vitamin deficiency, in which ATP is produced from fat metabolism, or when the conversion of lactate to glucose is slow because of liver or renal diseases or genetic or drug-induced defects in gluconeogenesis. Metabolic acidosis can also develop during pharmacological treatments, due to the exposition to chemical agents and in oncologic patients because cancer cells produce more lactate than normal cells even in aerobic conditions.

Lactate monitor is also important in diabetes control and rehabilitation.

In muscle, during exertion, pyruvate derived from glucose and glycogen is reduced to lactate, which is reoxidized and partially reconverted into glucose during rest (Cori cycle). The concentration of blood lactate is usually 1-2 mmol/L at rest, but can rise to over 20 mmol/L during intense exertion because of the switch of muscle cells to a anaerobic metabolism.

The classical explanation of lactate production was that this increased to provide supplementary anaerobically derived energy. However, currently, the predominant view is that the role of lactate formation as an energy source is of minor importance. Instead, it has been suggested that the increased lactate production are metabolic adaptations, which primarily serve to activate the aerobic ATP production [7]. Furthermore, the lactic acid is a strong stimulus to the secretion of anabolic hormones such as GH and testosterone. For this reason high intensity workout combined with short rest periods contributes to gain muscle mass. However, once a certain level of lactate concentration is reached, exhaustion occurs and there is a rapid decline in exercise capacity. Thus, in sport medicine it is used to monitor the maximum performance level of athletes.

On this basis, it is important to determine the amount of lactate in biological fluids (sweat, serum, plasma, saliva, urine, liquor, amniotic liquid . . . ) using simple, cheap, fast, precise and accurate methods.

The determination of lactate and pyruvate is usually performed in plasma or urine and it is based on enzymatic reactions, in particular LDH. The method is based on the determination of NADH using absorption spectroscopy or fluorescence spectroscopy. The drawbacks of enzymatic methods are both the need to operate at pH>8, and the instability of the enzyme and NADH cofactor.

Alternatively, the lactate is determined by gas chromatography (GC), liquid chromatography with mass spectrometric detection (LC-MS), high-performance liquid chromatography (HPLC). However, the cost of GC and HPLC instrumentation is typically high and measurements are long.

Blood analysis is an invasive practice, the sampling of blood has to be performed by a qualified medical staff with consideration for rigid hygienic regulations and infection risk.

The measurement of metabolites in media other than blood is becoming increasingly significant both because of the reasons reported above, and to avoid physical and mental strain especially for patients who have to control daily parameters, for people with problems in collecting blood (hemophiliacs, neonates, elderly people), for athletes to estimate their physical and biochemical conditions and to evaluate their training regime.

The use of sweat as an analytical sample dates back almost in seventies. The analysis of metabolites present in sweat is safe and simple. The analysis of sweat for electrolyte concentrations still remains the laboratory "gold standard" for the diagnosis of cystic fibrosis.

Advantages of sweat analysis are the ease of sample collection, no risk from infection, and that sampling can be frequently repeated with much less stress on the patient and athletes. Several authors shown a good correlation between the lactate concentration in sweat and in blood.

Based on the state of art, the determination of lactate in sweat is based on enzymatic assays, amperometric biosensors and on an electrochemiluminescence biosensor (ECL).

US Re.32016 proposes prior art techniques for the determination of lactate in blood with an invasive, high cost approach which uses the lactate oxidase (LO) enzyme. LO catalyzes the oxidation of lactate to pyruvate and hydrogen peroxide ($H_2O_2$). The amount of lactic acid is determined on the basis of the amount of $H_2O_2$ produced, detected using the ancillary reaction catalysed by peroxidase and colorimetry. In U.S. Pat. No. 3,573,171 the lactate determination is performer by LDH and glutamate-pyruvate transaminase, the coenzyme $NAD^+$, enzyme stabilizing agents and a trapping agent for pyruvate ion.

U.S. Pat. No. 4,254,222 describes the use of a tetrazolium salt, a pyridinic nucleotide, an electron carrier and the dehydrogenase enzyme specific for the enzyme that is determined in the assay (lactic and beta hydroxybutirric). U.S. Pat. No. 5,759,796 describes a method for the determination of lactic acid in organic materials of interest in the food chemistry, which uses LO, LDH and horseradish peroxidase, that measures the concentration of oxygen produced during oxidation of lactic acid using an amperometric electrode selective for oxygen. In U.S. Pat. No. 4,467,811 lactic acid is determined using polarography of $H_2O_2$ produced from lactic acid by the LO enzyme, while in U.S. Pat. No. 5,757,002 lactic acid is determined using infrared spectroscopy coupled to chemometric methods.

U.S. Pat. No. 7,319,018 describes a bio sensor strip for lactate, which includes a reference electrode and a working electrode. The two electrodes are deposited onto a support base electrically isolated. The working electrode is built up with inorganic graphite modified with immobilizer LO and an electron mediator. The graphite layer is deposited onto a silver layer of the working electrode. The reference electrode is built up by depositing silver chloride layer onto the silver layer of the reference electrode. In US 2009/0047177 lactate in biological fluids is measured using photometry.

JP2007127422 provides a method for measuring a component existing on the skin surface such lactic acid, by collecting the test material on an absorption patch having a component collection part, and reacting the collected test material with an enzymatic analysis reagent. The reagent contains lactate dehydrogenase, a diaphorase, nicotinamide-adenine-dinucleotide oxidant and a color reagent. The amount of lactic acid is measured by color development using a reflection light measuring device.

US2004141960 discloses a method of determining the risk of caries in a patient by determination of lactic acid and/or lactate produced by reaction of a signal-producing solution containing the enzymatic co-factor NAD.

CN101639446 discloses a method for detecting blood lactic acid in vitro by using a chemiluminescence method.

All these methods require very expensive enzymatic reagents and complex laboratory instrumentation. Several methods and instrumentation require well trained personnel. Thus, their use is restricted to clinical and high specialized laboratories. These methods are not applied to the determination of lactic acid to monitor athlete training or to simple, low-cost home care monitoring of lactate in biological fluids.

The present invention provides a method for simply measuring the lactic/lactate concentration, and to provide a non-invasive mean for effectively enabling a non-medical staff to perform easily health care.

Technical characteristics of the present invention, according to the aforesaid purposes, are clearly found in the content of the claims reported below.

OBJECT OF THE INVENTION

This goal is reached by a method for the determination of the content of lactic acid or lactate in biological fluids, which includes the providing of a biological sample, the providing of a selected amount of oxidant reagent able to reacts selectively with lactic acid or lactate, the mixing of the biological fluid and the oxidant reagent, the irradiating of the above mentioned mixing of the biological fluid and the oxidant reagent with UV light and the determining of the amount of lactic acid contained in the biological fluid by determining of the reduced species of the oxidant reagent.

The biological fluid can be available inside a container or a support, and the oxidant reagent is introduced in the said container or support.

Similarly, the biological fluid can be adsorbed onto paper or polymeric material or natural or synthetic tissue, and the oxidant reagent impregnates the above mentioned paper or polymeric material or natural or synthetic tissue, as well as the amount of oxidant reagent can be physically adsorbed or supported or chemically bound to paper or polymeric material or natural or synthetic tissue or other disposable support, and the sample of biological fluid can be placed onto the above mentioned support.

The biological fluid can be sweat, serum, plasma, saliva, urine, cerebrospinal fluid or amniotic liquid.

A second embodiment of this invention is aimed to set up simple kit of components which allows for the determining of the content of lactic acid or lactate in biological fluids according to the method of the invention.

These and other features of this invention are claimed and described below.

In order that the invention may be well understood it will now be described by way of illustration only with reference to the accompanying diagrammatic drawings in which.

DETAILED DESCRIPTION OF THE INVENTION

Figure 1:
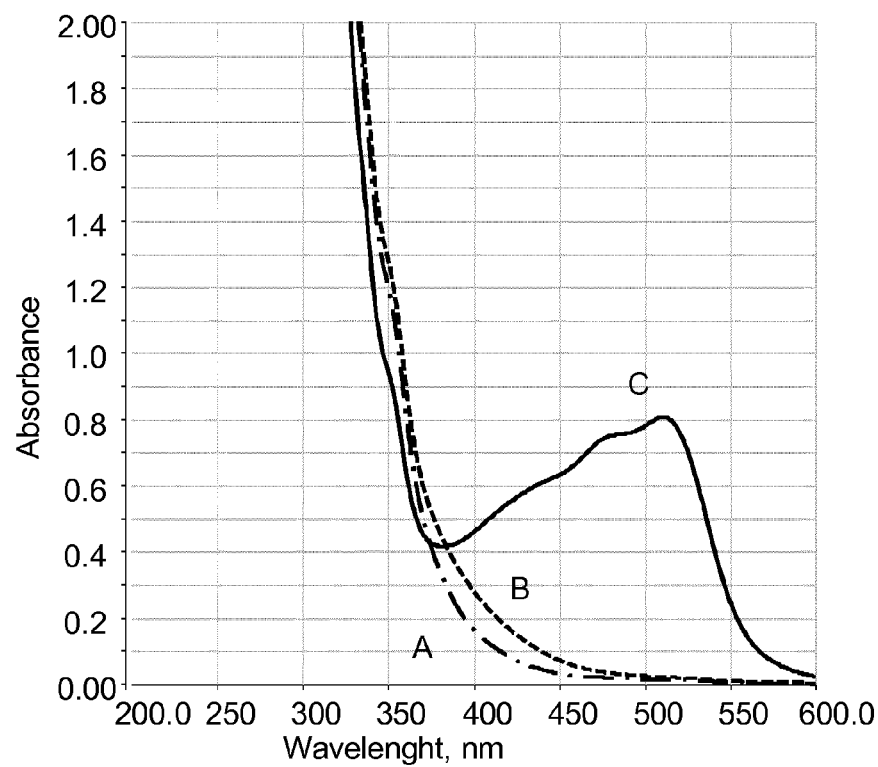
FIG. 1 shows UV/visible spectra of reagent solution with (B, C) or without (A) the addition of lactic acid, before (B) and after (C) irradiating with UV lamp.

Carboxylic acids such as citric acid and lactic acid in solution tend to be mildly oxidized if mixed with solutions containing an oxidant, such as $Fe^{3+}$, when exposed to light. According to the invention the irreversible reaction of oxidation is catalyzed irradiation with ultraviolet light (UV). The photochemical process consists in the reduction of $Fe^{3+}$ to $Fe^{2+}$, evolution of carbon dioxide and formation of oxidation products. In the case of lactic acid the reaction is as follows:

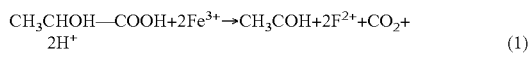

$$CH_3CHOH\text{---}COOH + 2Fe^{3+} \rightarrow CH_3COH + 2F^{2+} + CO_2 + 2H^+ \qquad (1)$$

According to a first preferred embodiment of this invention, this method uses this type of reaction to determine the lactic acid, using as a detection system of $Fe^{2-}$ produced the compound 1,10-phenanthroline:

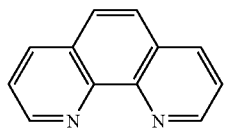

The reaction of $Fe^{2+}$ with 1,10-phenanthroline gives a red-orange colored complex, which allows the spectrophotometric measurement exploiting the absorption of a monochromatic light beam of wavelength in the range from 480-525 nm, preferably to 512 nm, which is the wavelength of maximum absorption of the $Fe^{2+}$-1,10-phenanthroline complex. This absorption is proportional to the concentration of the complex and, thus, by using calibration tables, to the concentration of lactate in the biological fluid.

In addition to 1,10-phenanthroline, other substances that may complex the Fe (II), and then allow the determination of Fe (II) in a simple and cheap way are:

hexacyanoferrate (III) or ferricyanide $[(Fe(III)(CN)_6]^{3-}$ (yellow) reacts with Fe(II) to give ferrous ferricyanide $Fe_3[(Fe(III)(CN)_6]_2$ (blue) that in the presence ferricyanide in excess gives a green colour solution;

The alfa'-dipyridyl [I] forms a soluble, red complex that absorbs at 525 nm.

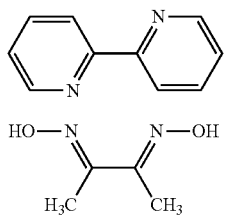

The dimethylglyoxime [II] reacts with ammonia solutions of Fe (II) forming a red, soluble complex. Nickel interferes in this essay to form a red insoluble complex.

The reagent composition and methods for detecting lactic acid and lactate described in this invention can be used in assays of conventional liquid. All reagents may be supplied in powder form and reconstituted with water immediately before use. Reagent composition of this type are clearly included in the present invention.

Suitable amounts of all components of the assay described in this invention may, of course, be embedded in a matrix of adsorbent material of different nature in order to give rise to qualitative or semi-quantitative assays of lactic acid or lactate. Typical materials suitable for the analysis of lactate or lactic acid are, for example, polymers, tissues and other materials are described in the following U.S. Pat. Nos. 3,092,465, 3,418,099, 3,418,083, 2,893,843, 2,8938,44, 2,912,309, 3,008,879, 3,802,842, 3,798,064, 3,298,739, 3,915,647, 3,917,453, 3,933,594, 3,936,357, 7,476,202B2 and other therein cited. Furthermore, the reagent composition and methods described in the present invention are of particular utility when the determination of the analyte is carried out on multilayer elements such as those described in U.S. Pat. Nos. 3,992,158, 7,871,568B2 and other therein cited.

The method described in this invention can be used to determine lactic acid or lactate in biological fluids (sweat, serum, plasma, liquor, urine, saliva, amniotic liquid . . . ) by means of various procedures of analysis and instrumental configurations:

a) Impregnating the Fe (III)/1,10-phenanthroline mixture onto known multilayer material such as those cited above. In this case a drop of the solution to be analyzed is placed in the plate wells with a drop of reagent, or onto filter paper or other material previously impregnated with the reagent at a concentration established. Only after irradiating with UV light an orange stain is formed due to the reduction of Fe (III) to Fe (II) by the lactate and the complexation of Fe (II) with 1,10-phenanthroline;

b) Adding the Fe (III)/1,10-phenanthroline mixture onto sorbent material on which sweat, for example, has been previously collected, or in other device for the collection of sweat, and irradiating with UV light;

c) spectrophotometric cuvette or in ELISA plates using a solution of Fe (III)/1,10-phenanthroline at a suitable concentration and UV light;

d) On line reaction using a flow injection system;

e) Liquid chromatography analysis (HPLC) coupled to on line post-column derivatization with Fe(III)/1,10-phenanthroline mixture and UV irradiating.

Advantageously, these preferred embodiments of the method of setting-up the reagent make possible to determine lactic acid using low cost reagents, stable for years.

The 1,10-phenanthroline costs, for example, 4.54 €/g. Thus, the cost of reagents, 1,10-phenanthroline and solution of Fe (III) 10 g/l is of the order of 0.002 €/Test Unit.

The cost of the enzymatic reagents is orders of magnitude higher and their stability is limited to 6-12 months.

We report below several examples which are not intended to be exhaustive of all possibilities of composition included in the scope according to this invention.

We tested in the lactate-Fe(III) reaction 5 lamps:

a) a low cost LED370E Ultra Bright Deep Violet LED (ThorLab, Germany);

b) UV lamp for nail gel curing;

c) high pressure Hg lamp;

d) low pressure Hg lamp.

e) USB lamp

Figure 6:
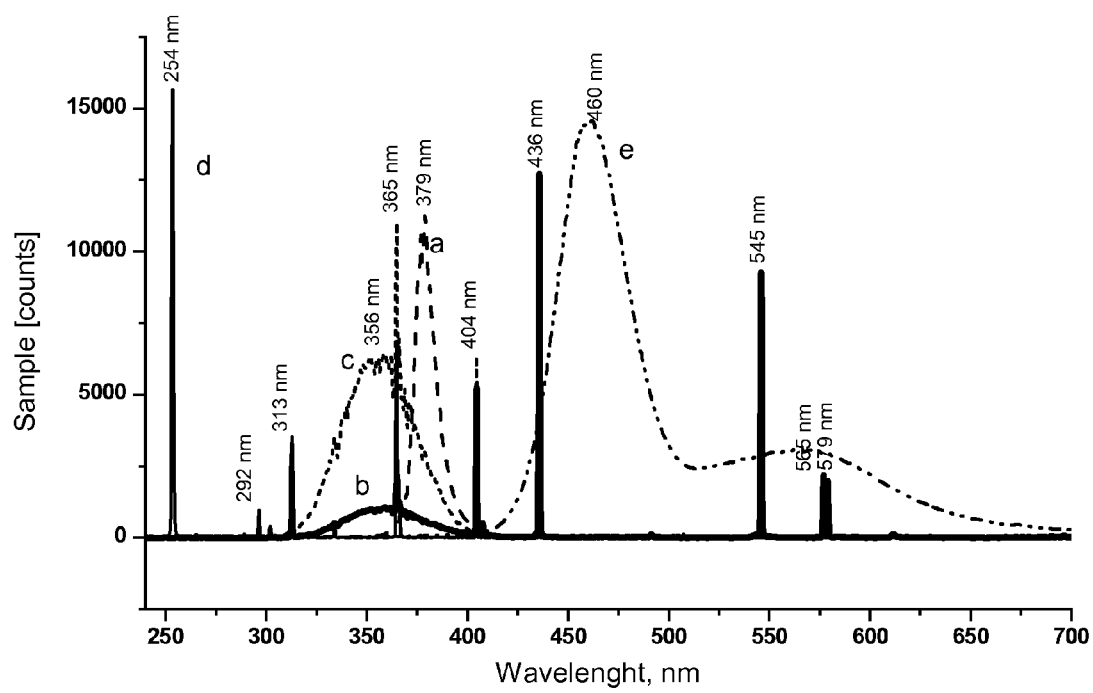
FIG. 6 shows the emission spectra of a) LED370E, b) UV lamp for nail gel curing, c) high pressure Hg lamp, d) low pressure Hg lamp, e) USB lamp.

FIG. 6 shows their emission spectra of a) a low cost LED370E Ultra Bright Deep Violet LED (ThorLab, Germany) (dash); b) UV lamp for nail gel curing (solid bold); c) high pressure Hg lamp (short dash); d) low pressure Hg lamp (thin solid); e) USB lamp (dash-dot-dot).

Table 1 summarizes the results expressed as variation of the signal of 3 mM lactate with respect to the blank measure solution (Δ in mV).

The best results were obtained with high pressure lamps and with LED370E. In the latter case a longer irradiation time (120 sec instead 60 sec) gave better results due to the small focused irradiation area and the need of homogenizing by stirring 1 mL of sample. This apparent drawback is an advantage when small drops of samples have to be irradiated in suitable devices.

TABLE 1

| Lamp description | Δ (mV) |
|---|---|
| LED370E (60 sec) | 58 |
| LED370E (120 sec) | 74 |
| UV lamp for nail gel curing (high pressure). | 92 |
| High pressure Hg lamp, | 77 |
| Low pressure Hg lamp | 40 |
| USB lamp | 0 |

USB lamp having an emission spectrum in the 400-700 nm range (visible) did not show any activation ability. Thus the best irradiation wavelength to activate the lactate/Fe(III) reaction is in the range 300-400 nm.

Example n. 1. Test in Cuvette Using Colorimetric/Spectrophotometric Analysis: Analysis of Lactate in Human Sweat A) Preparation of Standard Solutions and Reagents for Calibration Curve.

For the spectrophotometric/colorimetric assay the following solutions are needed:

a) Standard solution of 15 mg/ml (15,000 ppm, or 83.3 mM) 1,10-phenanthroline. This solution is prepared by dissolving 75 mg of powder in 1 ml of ethanol and adding 4 ml of water;

b) Standard solution of 10 g/l (10,000 ppm, or 179 mM) Fe (III) in 0.1 M $HNO_3$;

c) Standard solution of 1.31 M lactic acid (obtained by diluting 100 μl of lactic acid L6402 Sigma-Aldrich-Fluka, molecular weight 90.08, density=1.2 mg/ml in 900 μl of deionized water).

a) and b) solutions are diluted and mixed in quartz cuvette in order to get a solution with the following composition: 5 mM 1,10-phenanthroline+5 mM Fe(III) ((d) solution).

Thus, increasing concentrations of lactic acid are added to solution d) by performing suitable dilutions of solution c). Solution d) containing lactic acid (0.3 mM for example) is irradiated with UV lamp of type b) for 60 seconds.

FIG. 1 shows UV/visible spectra of solution d) (A curve) of solution d)+0.3 mM lactic acid before (B curve) and after (C curve) irradiating with a UV lamp of type b) for 60". Solution d) without lactic acid is yellow. After the addition of 0.3 mM lactic acid and irradiation with a UV lamp of type b) for 60" the solution becomes orange-red.

Figure 2:
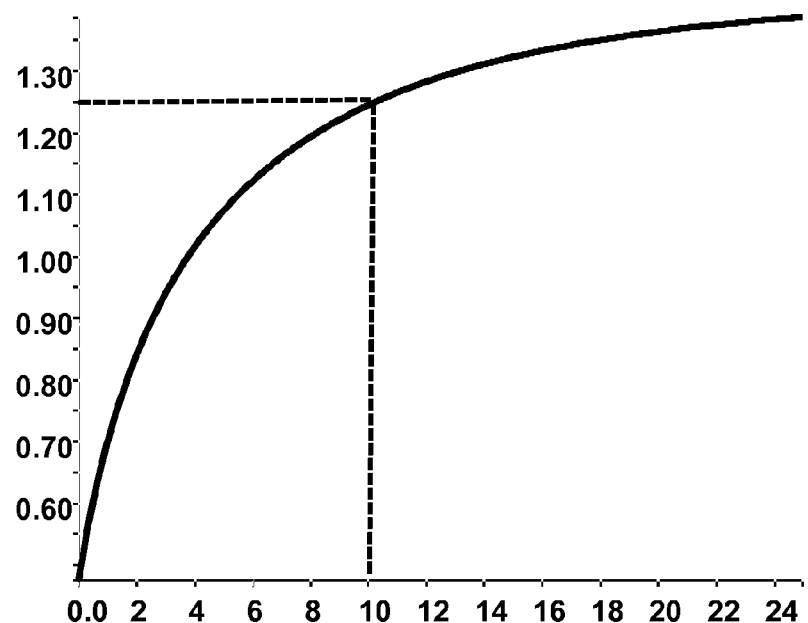
FIG. 2 shows the kinetics (absorbance at 512 nm vs. reaction time) of the reaction between 0.3 mM lactic acid and the reagent solution after irradiating with a UV lamp of type b) (see FIG. 6) for 60 seconds.

FIG. 2 shows the kinetics (absorbance at 512 nm vs. reaction time) of the reaction between 0.3 mM lactic acid and the reagent solution (d) after irradiating with a UV lamp of type b) for 60 seconds. From FIG. 2 it results that the absorbance value after 10 min reaches 90% of the maximum plateau value. Thus, 10 min reaction time has been selected to perform the calibration curve.

Figure 3:
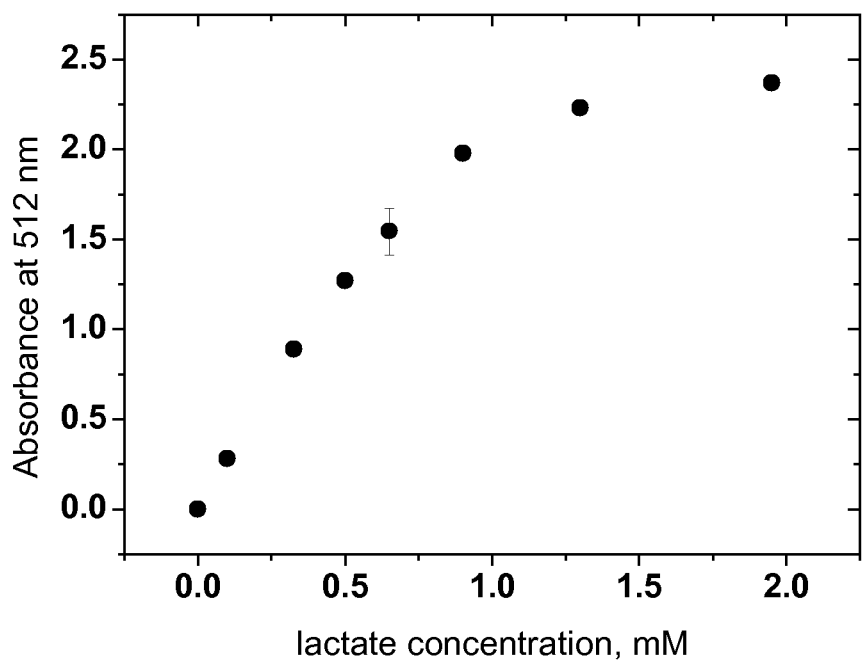
FIG. 3 shows the calibration curve obtained by plotting the absorbance values at 512 nm of solutions containing increasing concentration of lactic acid after reacting with the reagent solution and UV irradiating.

FIG. 3 shows the calibration curve obtained by plotting the absorbance values at 512 nm of solutions containing increasing concentration of lactic acid after reacting with the reagent solution d) and UV irradiation with UV lamp of type b) for 60", analyzed 10 min after their preparation.

The method shows a linear dynamic range between 0.05 and 1 mM lactic acid (in the linear part of the fitting parameters are: slope=2.21 $mM^{-1}$ (SD=0.116), $R^2$=0.9864, N=6). The limit of quantification (LOQ) is 0.05 mM. The precision is 3.1% (percent coefficient of variation).

The proposed method was applied to the determination of lactic acid in sweat of athletes subjected to physical exercise.

The concentration of lactate in plasma is generally less than 2 mM, while in sweat it ranges between 10 and 15 mM or more. A part of this comes from the metabolism of sweat glands as a product of glycolysis. The other part comes from the plasma lactate and, accordingly, follows lactate variations as a result of physical activity.

B) Sample Preparation a) Each determination requires from 20 to 500 mg of sweat. The eccrine sweat is collected during exercise from the lower back, for example, but it can be collected in other areas of the body. In the specific example, sweat is collected onto filter paper (42 Whatman ashless, n. 1442070, diameter 70 mm) kept in position during exercise by means of an adhesive patch during the time established for the sampling. Alternatively, the sweat can be collected with other methods already adopted in the medical practice, for example through capillary devices;

b) In the case of the sampling method that uses filter paper, the sweat is extracted with 1.5-3 ml of deionized water to obtain a 1:10 dilution, approximately. If sweat is collected as is using capillaries, it must be diluted about 10 times with deionized water (100 μl+900 μl of water);

c) 100 μl of diluted sweat solution are added to 900 μl of reagent (i.e. the 5 mM 1,10-phenanthroline+5 mM Fe(III) mixture, solution d), thus obtaining a concentration value included in the dynamic linear range of the method (0.05-1 mM).

d) The diluted sweat+reagent (solution d) mixture is then transferred into a cuvette for spectrophotometric analysis (volume 1 mL), and irradiated with a UV lamp of type b) for 60". After 10 minutes reaction time the absorbance at 512 nm of the solution is read in a spectrophotometer or colorimeter.

e) The spectrophotometer is set at a wavelength of 512 nm and calibrated with a blank solution (solution (d) without sweat sample added, irradiated for 60" with the UV lamp of type b), analyzed after 10 min from irradiation). After this, the absorbance of the sample solution is measured.

The measurement duration is less than 2 minutes.

Table 2 shows as an example the results of the concentration of lactic acid found in two samples of human sweat, compared with the value of the concentration of lactic acid found by chromatographic method (HPLC). The values were corrected taking into account the dilution factor (10× 10=100).

TABLE 2

| Sample | Lactic acid concentration (mM) (o-phen/Fe(III)/UV method) | Lactic acid concentration (mM) (HPLC method) |
|---|---|---|
| Sweat 1 (abdominals) | 16.4 | 18.7 |
| Sweat 2 (cyclette) | 49.6 | 43.0 |

The results show an accuracy of 88% and 115% for the two samples 1 and 2, respectively. These values of accuracy are good, taking into account that currently no certified method for sweat analysis are reported.

Example n. 2. Test in Cuvette Using Colorimetric/Spectrophotometric Analysis: Analysis of Lactate in Human Saliva A) Preparation of Standard Solutions and Reagents for Calibration Curve.

For the spectrophotometric/colorimetric assay the following solutions are needed:

a) Standard solution of 15 mg/ml (15,000 ppm, or 83.3 mM) 1,10-phenanthroline. This solution is prepared by dissolving 75 mg of powder in 1 ml of ethanol and adding 4 ml of water;

b) Standard solution of 10 g/l (10,000 ppm, or 179 mM) Fe (III) in 0.1 M $HNO_3$;

c) Standard solution of 1.31 M lactic acid (obtained by diluting 100 μl of lactic acid L6402 Sigma-Aldrich-Fluka, molecular weight 90.08, density=1.2 mg/ml in 900 μl of deionized water).

a) and b) solutions are diluted and mixed in quartz cuvette in order to get a solution with the following composition: 5 mM 1,10-phenanthroline+5 mM Fe(III) ((d) solution).

Thus, increasing concentrations of lactic acid are added to solution d) by performing suitable dilutions of solution c). Solution d) containing lactic acid (0.3 mM for example) is irradiated with a UV lamp of type b) for 60 seconds.

B) Sample Preparation a) Each determination requires 100 a 200 microliters of saliva.

b) 100 μl of saliva are added to 900 μl of reagent (i.e. the 5 mM 1,10-phenanthroline+5 mM Fe(III) mixture, solution d), thus obtaining a concentration value included in the dynamic linear range of the method (0.05-1 mM).

c) The saliva+reagent (solution d) mixture is then transferred into a cuvette for spectrophotometric analysis (volume 1 mL), and irradiated with a UV lamp of type b) for 60". After 10 minutes reaction time the absorbance at 512 nm of the solution is read in a spectrophotometer or colorimeter.

d) The spectrophotometer is set at a wavelength of 512 nm and calibrated with a blank solution (solution (d) without sweat sample added, irradiated for 60" with the UV lamp of type b), analyzed after 10 min from irradiation). After this, the absorbance of the sample solution is measured.

The measurement duration is less than 2 minutes.

The lactate concentration value found in saliva sample was 2.1±0.07 mM, taking into account the dilution correction factor (1:10).

Example n. 3. Qualitative Analysis of Lactic Acid Using Disposable Device

Five squares were cut from a common patch, impregnated with 200 μl of the reaction mixture (ie the 5 mM 1,10-phenanthroline+5 mM Fe (III) mixture, solution d) and were allowed to dry. Then 100 μl of solutions of increasing concentration of lactic acid (0, 0.325, 3.25, 6.5, 65 mM) were deposited on each square, irradiated with a UV light of type b) for 60".

More intense colors correspond to samples containing higher concentrations of lactic acid. This procedure can be used in a qualitative manner to show, for example, an exceeding level of lactic acid in sweat during training, compared to a threshold value, or in a quantitative manner wherever the mixture can be physically adsorbed or chemically bound to a support and integrated in any disposable diagnostic test strips for portable reader (similar to those used for the measurement of blood glucose in diabetics), or by processing the image in terms of color intensity after scanning.

According to a further way of implementing this invention, a suitable concentration of the solution of Fe (III) required for the photochemical reaction of lactate described in this invention can, of course and conveniently, be incorporated in a matrix of sorbent material to get disposable test strips suitable for the quantitative determination of lactic acid or lactate with physico-chemical techniques, such as electrochemical techniques.

According to a preferred set up, disposable electrochemical strips soaked with the reagent solution and the biological fluid to be analysed are appropriately irradiated with UV light and then subjected to electrochemical tests using portable meters commercially available, modified in order to provide a sample holder to irradiate the sample with UV light for a selected time.

Figure 4:
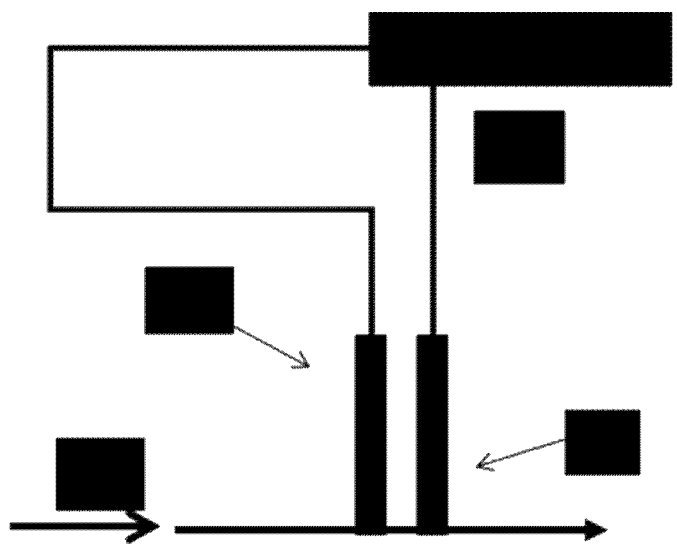
FIG. 4 shows the diagram of the electrochemical detector, according to an embodiment of the invention.

Electrochemical techniques has been successfully used for the determination of lactic acid or lactate in biological fluids, such as sweat, serum, plasma, urine, saliva, using various analytical procedures and instrumental configurations:

a) In a potentiometric cell built with a platinum electrode and a calomel reference electrode, adding a suitable concentration of the Fe(III) solution to the lactic acid solution, and carrying out the measurement after irradiating with UV light the mixture;

b) In a potentiometric cell built with a platinum microelectrode and a reference Ag/AgCl microelectrode in series in a flow injection system (FIG. 4), adding a suitable concentration of the Fe(III) solution to the lactic acid solution, and carrying out the measurement after irradiating with UV light the mixture;

c) Supporting a suitable concentration of the Fe(III) solution onto an impregnating or multilayer material. In this case a drop of the sample solution containing lactate is added/sucked for capillarity on the material previously impregnated with the reagent.

Example n. 4. Test in Potentiometric Cell: Analysis of Lactate in Human Sweat

A) Preparation of Standard Solutions and Reagents for Calibration Curve.

The potentiometric assay needs the following solutions a) Standard solution of 10 g/l (10,000 ppm, or 179 mM) Fe (III) in 0.1 M $HNO_3$;

b) Standard solution of 3.7 M lactic acid (obtained by diluting 5 g of lactic acid from Carlo Erba in 15 ml total deionized water, molecular weight 90.08, density=1.21 g/mL). Solution a) must be suitably diluted in order to obtain a 5 mM Fe(III) solution (solution c).

Thus, increasing concentrations of lactic acid obtained by appropriate dilutions of the solution b) are added to solution c).

Each solution c), containing increasing concentrations of lactic acid, are irradiated with a UV lamp of type c) for 60 seconds.

The measure system is a potentiometric cell built with a calomel reference electrode ($Hg|Hg_2Cl_2|Cl^-$) and a platinum working electrode connected to a digital reader of the difference of potential in mV.

Figure 5:
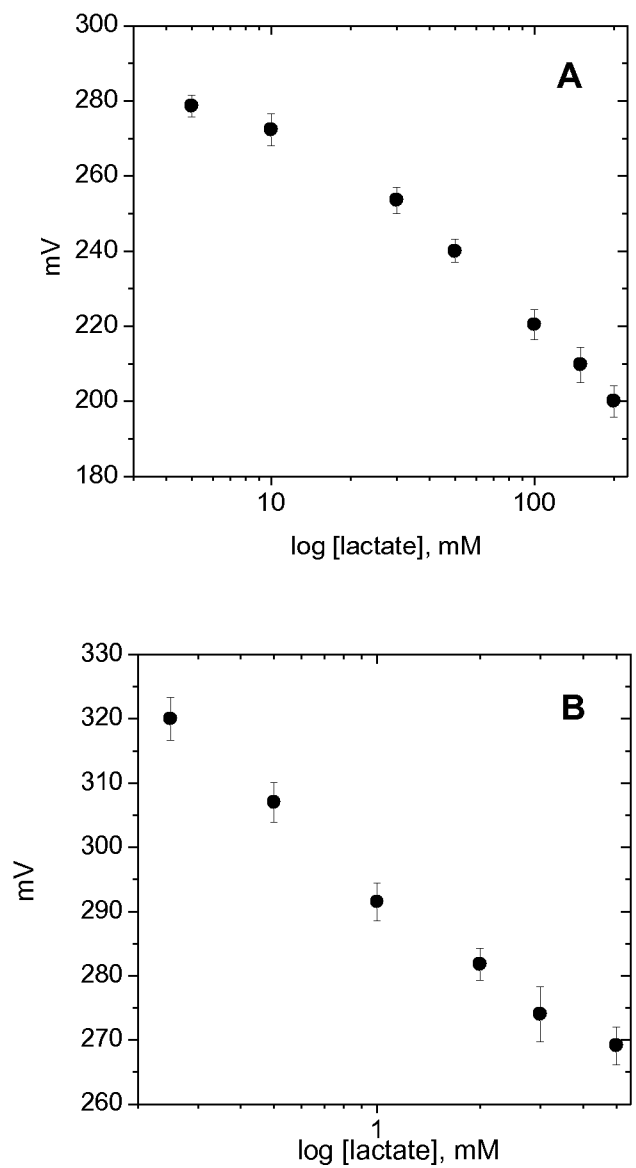
FIG. 5 shows the calibration curves obtained by plotting the difference of potential values (mV) of solutions containing increasing concentration of lactic acid after reacting with the reagent solution and UV irradiating, the lactate concentration being 1-150 mM (FIG. 5A) and 0.1-5.0 mM (FIG. 5B).

FIG. 5 shows the calibration curve obtained from the values of the difference of potential (mV) recorded in 8 solutions containing increasing concentration of lactic acid (0, 0.25, 0.5, 1, 2, 3, 5, 10, 50, 100, 150, 200 mM) after the reaction with the solution c), irradiated with a W UV lamp of type c) for 60" and analyzed immediately after preparation.

The calibration curve (difference of potential vs. the logarithm of the concentration of lactate) shows a discontinuity in the linearity between 5 and 10 mM and is linear between 0.25 and 10 mM lactate (FIG. 5B) and between 10 and 200 mM acid lactic (FIG. 5A). The latter is the range of lactate concentrations typically found in human sweat at rest and during intense exercise. To detect lower concentrations for example in human blood is appropriate to use the calibration curve of FIG. 5B.

Table 3 summarizes the parameters of data fitting in the range 0.25-5 and 5-10 mM lactate of calibration curves (difference of potential vs. the logarithm of the concentration of lactate).

TABLE 3

| Range | Intercept (SD) | slope (SD) | $R^2$ |
|---|---|---|---|
| 0.25-10 mM | 294.4 (0.94) | 39.6 (2.13) | 0.9857 |
| 10-200 mM | 349.2 (1.9) | 64.6 (1.02) | 0.9990 |

SD = standard deviation.

The limit of quantification of lactate (LOQ) is 0.1 mM. The precision is 2.2% expressed as percent coefficient of variation (CV %).

Example n. 5. Analysis of Lactate by Flow Injection System (FIA) and Potentiometric Detector: Analysis of Lactate in Human Sweat A) Preparation of Standard Solutions and Reagents for Calibration Curve.

The potentiometric assay needs the following solutions
  a) Standard solution of 10 g/l (10,000 ppm, or 179 mM) Fe (III) in 0.1 M $HNO_3$;
  b) Standard solution of 3.7 M lactic acid (obtained by diluting 5 g of lactic acid from Carlo Erba in 15 ml total deionized water, molecular weight 90.08, density=1.21 g/mL). Solution a) must be suitably diluted in order to obtain a 5 mM Fe(III) solution (solution c). Thus, increasing concentrations of lactic acid obtained by appropriate dilutions of the solution b) are added to solution c).

Each solution c), containing increasing concentrations of lactic acid, are irradiated with a UV lamp of type c) for 60 seconds.

The measure system employed is a potentiometric cell schematized in FIG. 5, with an on line injection system of the liquid sample (4) and a waste tubing (5), built with a silver reference microelectrode (Ag/AgCl) (1) and a platinum working microelectrode (2) (models 16-702 and 16-705 modified, respectively, Microelectrodes, Inc., Bedford, N.H.) electrically connected to a digital reader of the difference of potential in mV (3).

The calibration curve is obtained by plotting the values of the difference of potential (mV) measured in various solutions containing increasing concentration of lactic acid (between 0 and 10 mM) after reacting with the solution c) prepared at two different Fe (III) concentration levels (1 and 5 mM), irradiated with a W UV lamp of type c) for 60" and injected into the system just after preparation.

Calibration curves (difference of potential vs. the logarithm of the concentration of lactate) are linear between 0.1 and 5 mM lactate. Table 3 summarizes the values of the linear fitting of data.

The limit of quantification of lactate (LOQ) is 0.1 mM. The precision is 2.2% expressed as percent coefficient of variation (CV %).

Table 4 reports the parameters of data fitting of calibration curve (difference of potential vs. the logarithm of the concentration of lactate) in the range 0.1-5 mM lactate

TABLE 4

| Fe(III) concentration | Intercept (SD) | Slope (SD) | $R^2$ |
|---|---|---|---|
| 1 mM | 544 (1.1) | 44.8 (2.0) | 0.9846 |
| 5 mM | 607.1 (1.6) | 38.5 (2.6) | 0.9689 |

SD = standard deviation.

The proposed method has been applied to the determination of lactic acid in sweat of athletes subjected to physical exercise.

B) Sample Preparation
  a) Each determination takes from 20 to 500 mg of sweat. The eccrine sweat is collected during exercise from the lower back, for example, but it can be collected in other areas of the body. In the specific example, sweat is collected onto filter paper (42 Whatman ashless, n. 1442070, diameter 70 mm) kept in position during exercise by means of an adhesive patch during the time established for the sampling. Alternatively, the sweat can be collected with other methods already adopted in medical practice, for example using capillary devices;
  b) In the case of the sampling method that uses filter paper, the sweat is extracted with 1.5-3 ml of deionized water to obtain a 1:10 dilution, approximately. If sweat is collected as is using capillaries, it must be diluted about 10 times with deionized water (100 μl+900 μl of water);
  c) 5.6 μl of reagent (i.e. 1 mM Fe(III) are added to 1 ml of diluted sweat solution.
  d) Then, the diluted sweat+1 mM Fe(III) mixture is irradiated with a W UV lamp of type c) for 60" and injected in the FIA apparatus that includes the two microelectrodes. The difference of potential value is recorded by a PC.
  e) The procedure also requires the measurement of a blank solution (1 or 5 mM Fe(III) solution without sweat sample added), irradiated with a W UV lamp of type c) for 60" and analyzed immediately after irradiation. The measure duration is less than 1 minute.

This instrumental configuration has the advantage of requiring only a small volume of sample solution (0.5-1 ml of diluted sweat solution)

Table 5 shows as an example the results of the analysis of lactic acid found in three samples of human sweat, compared with the value of the concentration of lactic acid found in the same samples with the chromatographic method (HPLC). The values were corrected taking into account the dilution factor (10×10=100).

TABLE 5

| Sample | Lactic acid concentration (mM) Fe(III)/UV Electrochemical method | Lactic acid concentration (mM) HPLC method |
|---|---|---|
| sweat 1 | 8.6 | 10.4 |
| sweat 2 | 16.0 | 16.8 |
| sweat 3 | 15.6 | 17.3 |

The results show an accuracy ranging between 83 and 95%.

Example n. 6. Analysis of Lactate by Flow Injection System (FIA) and Potentiometric Detector: Analysis of Lactate in Human Urina A) Preparation of Standard Solutions and Reagents for Calibration Curve.

This potentiometric assay needs the same solutions reported in Example n. 5.

The determination of lactate in urine is performed by diluting the urine 1:1 with deionized water using the analyte additions technique, i.e. by spiking the diluted urine samples with known amounts of analytes. The analyte additions curve is obtained by plotting the values of the difference of potential (mV) as a function of lactic acid concentration found by injecting the solutions after UV irradiation with a W UV lamp of type c) for 60".

B) Sample Preparation a. Increasing concentrations of lactate from standard solution in the range 0-5 mM are added to 1 ml of diluted urine (1:1). Thus, 28 µl of reagent solution (i.e. 5 mM Fe(III)) are added.

b. The diluted urine (spiked or not with lactate standard solution)+5 mM Fe(III) mixture is irradiated with a W UV lamp of type c) for 60" and injected in the FIA system that includes the two reference and working electrodes. Thus, for each solution the difference of potential values are measured.

The concentration of lactate in the urine sample was determined from the intercept value on x axis of the linear plot difference of potential (mV) vs. lactate concentration added (analyte additions technique).

In the urine sample examined from healthy volunteer the endogenous concentration of lactate was below the detection limit (0.03 mM) (curve fitting parameters: intercept of y axis=5.67±2 mM; slope=−5.3±0.7, $R^2$=0.926).

The invention claimed is:

1. Method for the determining of content of lactic acid or lactate in biological fluids including the following steps:
providing a biological fluid,
providing a selected amount of Fe(III), or other redox couple oxidized metal/reduced metal oxidant reagent able to react selectively with lactic acid or lactate,
mixing of the biological fluid and the oxidant reagent;
irradiating of said mixing of the biological fluid and the oxidant reagent with UV light in the wavelength range of 280-400 nm;
determining the amount of lactic acid contained in the biological fluid by determining of the reduced species of the oxidant reagent,
by keeping at a constant difference of potential, at a value specific of the redox couple, a cell formed by two shorted electrodes buried into said mixing of said biological fluid and said oxidant reagent after irradiation with UV light, and
by measuring the impedance of said cell.

2. The method according to claim 1, in which the biological fluid is available inside a container or a support, and the oxidant reagent is introduced in the said container or support.

3. The method according to claim 2, in which the biological fluid is adsorbed onto paper or polymeric material or natural or synthetic tissue, and the oxidant reagent impregnates said paper or polymeric material or natural or synthetic tissue.

4. The method according to claim 1, in which the amount of oxidant reagent is physically adsorbed or supported or chemically bound to paper or polymeric material or natural or synthetic tissue or other disposable support, and the sample of biological fluid is placed onto said support.

5. The method according to claim 1, in which said biological fluid is sweat, serum, plasma, saliva, urine, cerebrospinal fluid or amniotic liquid.

6. The method according to claim 4, in which said mixing of the biological fluid and the oxidant reagent is irradiated with UV light in the wavelength range of 300-400 nm.

7. Method for the determining of content of lactic acid or lactate in biological fluids including the following steps:
providing a biological fluid,
providing a selected amount of Fe(III), or other redox couple oxidized metal/reduced metal oxidant reagent able to react selectively with lactic acid or lactate,
mixing of the biological fluid and the oxidant reagent;
irradiating of said mixing of the biological fluid and the oxidant reagent with UV light in the wavelength range of 280-400 nm;
determining the amount of lactic acid contained in the biological fluid by determining of the reduced species of the oxidant reagent,
by measuring the electrochemical potential of a cell among two electrodes buried into said mixing of said biological fluid and said oxidant reagent after irradiation with UV light.

8. The method according to claim 7, in which the biological fluid is available inside a container or a support, and the oxidant reagent is introduced in the said container or support.

9. The method according to claim 8, in which the biological fluid is adsorbed onto paper or polymeric material or natural or synthetic tissue, and the oxidant reagent impregnates said paper or polymeric material or natural or synthetic tissue.

10. The method according to claim 7, in which the amount of oxidant reagent is physically adsorbed or supported or chemically bound to paper or polymeric material or natural or synthetic tissue or other disposable support, and the sample of biological fluid is placed onto said support.

11. The method according to claim 7, in which said biological fluid is sweat, serum, plasma, saliva, urine, cerebrospinal fluid or amniotic liquid.

12. The method according to claim 10, in which said mixing of the biological fluid and the oxidant reagent is irradiated with UV light in the wavelength range of 300-400 nm.

13. Kit for the determination of the content of lactic acid or lactate in biological fluids including the following items:
a container/support for the arrangement of a sample of biological fluid,
a container/support for the arrangement of a selected amount of Fe(III), or other redox couple oxidized metal/reduced metal oxidant reagent able to selectively react with lactic acid or lactate,
a container/support for the mixing of the biological fluid and the oxidant reagent;
irradiation means of UV light of wavelength of 280-400 nm of said mixing of the biological fluid and the oxidant reagent,
a couple of electrodes buried/in contact with the support forming a cell;
an apparatus for the measurement of the current density flowing between said shorted electrodes kept at a constant difference of potential value specific of the redox couple buried into said mixing of the biological fluid and the oxidant reagent after irradiation with UV light; and
an apparatus for the measurement of the impedance of said built-up cell within said two shorted electrodes kept at a constant difference of potential value.

14. Kit according to claim 13, in which the container/support for the arrangement of a sample of biological fluid is paper or polymeric material or natural or synthetic tissue or other disposable support.

15. Kit according to claim 13, in which the container/support for the arrangement of the oxidant reagent is paper or polymeric material or natural or synthetic tissue or other disposable support on which said oxidant reagent is physically adsorbed or supported or chemically bound.

16. Kit according to claim 15, in which said apparatus for the UV light irradiation emits radiations of wavelength 300-400 nm.

17. Kit for the determination of the content of lactic acid or lactate in biological fluids including the following items:
- a container/support for the arrangement of a sample of biological fluid,
- a container/support for the arrangement of a selected amount of Fe(III), or other redox couple oxidized metal/reduced metal oxidant reagent able to selectively react with lactic acid or lactate,
- a container/support for the mixing of the biological fluid and the oxidant reagent;
- irradiation means of UV light of wavelength of 280-400 nm of said mixing of the biological fluid and the oxidant reagent,
- a couple of electrodes forming a cell buried/in contact with said support and said mixture of biological fluid and oxidant reagent after irradiation with UV light, and
- a differential potentiometer for the measurement of the electrochemical potential between said two electrodes.

18. Kit according to claim 17, in which the container/support for the arrangement of a sample of biological fluid is paper or polymeric material or natural or synthetic tissue or other disposable support.

19. Kit according to claim 17, in which the container/support for the arrangement of the oxidant reagent is paper or polymeric material or natural or synthetic tissue or other disposable support on which said oxidant reagent is physically adsorbed or supported or chemically bound.

20. Kit according to claim 19, in which said apparatus for the UV light irradiation emits radiations of wavelength 300-400 nm.

\* \* \* \* \*